United States Patent
Royo Bargués

(10) Patent No.: US 11,214,593 B2
(45) Date of Patent: Jan. 4, 2022

(54) ANTICANCER PEPTIDES AND USES THEREOF

(71) Applicant: SUIGENERIS FARMACOSMETICS, S.L., Barcelona (ES)

(72) Inventor: Teresa Royo Bargués, Barcelona (ES)

(73) Assignee: SUIGENERIS FARMACOSMETICS, S.L., Barcelona (ES)

( * ) Notice: Subject to any disclaimer, the term of this patent is extended or adjusted under 35 U.S.C. 154(b) by 0 days.

(21) Appl. No.: 16/753,627

(22) PCT Filed: Oct. 4, 2018

(86) PCT No.: PCT/EP2018/077033
§ 371 (c)(1),
(2) Date: Apr. 3, 2020

(87) PCT Pub. No.: WO2019/068822
PCT Pub. Date: Apr. 11, 2019

(65) Prior Publication Data
US 2020/0239520 A1    Jul. 30, 2020

(30) Foreign Application Priority Data
Oct. 5, 2017    (EP) .................................... 17382667

(51) Int. Cl.
| A61K 38/08 | (2019.01) |
| C07K 7/06 | (2006.01) |
| A61K 47/62 | (2017.01) |
| A61K 38/00 | (2006.01) |

(52) U.S. Cl.
CPC ................ C07K 7/06 (2013.01); A61K 38/08 (2013.01); *A61K 38/00* (2013.01); *A61K 47/62* (2017.08)

(58) Field of Classification Search
CPC ........ A61K 38/03; A61K 38/08; A61K 47/42; A61K 47/62; A61K 47/64; C07K 4/00; C07K 7/06; C07K 2319/00
See application file for complete search history.

(56) References Cited

U.S. PATENT DOCUMENTS

2014/0011739 A1* 1/2014 Klatzmann ............... A61P 3/10
                                                             514/5.9

FOREIGN PATENT DOCUMENTS

| WO | WO 2012/001169 A1 | 1/2012 |
| WO | WO 2014/079943 A1 | 5/2014 |

OTHER PUBLICATIONS

Kuzmenkov et al. Variability of Potassium Channel Blockers in Mesobuthus eupeus Scorpion Venom with Focus on Kv1.1. The Journal of Biological Chemistry. May 8, 2015, vol. 290, No. 19, pp. 12195-12209. (Year: 2015).*

Sakamoto et al. Identification and characterization of novel calcium-binding proteins of Dictyostelium and their spatial expression patterns during development. Development, Growth & Differentiation. 2003, vol. 45, pp. 507-514. (Year: 2003).*

SCORE—View Sequence Detail(s) for U.S. Appl. No. 13/843,766. Application published on Jan. 9, 2014 as USPAP 2014/0011739. (Year: 2014).*

International Search Report and Written Opinion dated Jan. 4, 2019 for PCT Application No. PCT/EP2018/077033, 21 pages.

Copolovoci, et al., "Cell-Penetrating Peptides: Design, Synthesis, and Applications", ACS Nano 2014, vol. 8, No. 3, pp. 1972-1994.

Ford, et al., "Protein transduction: an alternative to genetic intervention?" Gene Therapy 2001, vol. 8, pp. 1-4.

Schmidt, et al., "Liposome-Based Adjuvants for Subunit Vaccines: Formulation Strategies for Subunit Antigens and Immunostimulators", Pharmaceutics Mar. 2016, vol. 8, No. 1, pp. 1-22.

Marcelino, et al., "Evolutionary Dynamics of chloroplast genomes in lowlight: a case study of the endolithic green alga Ostrebium quekettii", Database CA [online] Chemical Abstracts Service, Columbus Ohio USA; XP002787113, retrieved from STN Database accession No. 2016:2031716 abstract; compounds 2047382-91-0, (2016).

Kuzmenkov, et al., "Variability of Potassium Channel Blockers in Mesobuthus eupeus Scorpion venom with Focus on Kv1.1", Database CA [online] Chemical Abstracts Service, Columbus Ohio USA; XP002787114, retrieved from STN Database accession No. 2015:801076 abstract; compounds 1704781-39-4. (2015).

Infante, et al., "Molecular Characterization and Expression Analysis of Five Different Elongation Factor 1 Alpha Genes in the flatfish Senegalese sole (*Solea senegalensis* Kaup): Differential Gene Expression and Thyroid Hormones Dependence during Metamorphosis", Database CA [online] Chemical Abstracts Service, Columbus Ohio USA; XP0027B7115, retrieved from STN Database accession No. 2008:629737 abstract; compounds 152053-41-4. (2008).

(Continued)

Primary Examiner — Jeffrey E. Russel
(74) Attorney, Agent, or Firm — Squire Patton Boggs (US) LLP

(57) ABSTRACT

The present invention provides a peptide of formula (I), or a pharmaceutically acceptable salt thereof, wherein the N-terminal group of the peptide is a monoradical of formula —$NHR_1$; the C-terminal group of the peptide is a monoradical of formula —$C(O)$—$R_2$; $R_1$ is a monoradical selected from hydrogen and —$C(O)$—$(C_1$-$C_{20})$alkyl; $R_2$ is a monoradical selected from —OH and —$NR_3R_4$ radical; $R_3$ and $R_4$ are independently selected from hydrogen and ($C_1$-$C_{10}$)alkyl; "a" to "j" are integers from 0 to 1, provided that at least one of "a" to "j" is 1; and $X_1$ represents any amino acid. The present invention also provides conjugates and compositions comprising the peptide of formula (I). The peptide can be used in the treatment or prevention of neoplastic diseases such as pancreatic cancer.

$$C_a C_b C_c C_d C_e FEX_1 SKYC_f C_g C_h C_i C_j \quad (I)$$

16 Claims, 2 Drawing Sheets

Specification includes a Sequence Listing.

(56) References Cited

OTHER PUBLICATIONS

Pel, et al., "Genome Sequencing and analysis of the versatile cell factory Aspergillus niger CBS 513.88", Database CA [online] Chemical Abstracts Service, Columbus Ohio USA; XP002787116, retrieved from STN Database accession No. 2007:344358 abstract; compounds 908431-96-0, (2007).

Ogata, et al., "Genome Sequence of Rickettsia bellii illumiates the role of amoebae in gene exchanges between intracellular pathogens", Database CA [online] Chemical Abstracts Service, Columbus Ohio USA; XP002787117, retrieved from STN Database accession No. 2006:520953 abstract; compounds 887184-37-4, (2006).

Ishida, et al., "Aspergillus niger ornithine N-5 oxygenase and peptide synthetase genes and use for biosynthesis of ferrichrome and peptides", Database CA [online] Chemical Abstracts Service, Columbus Ohio USA; XP002787118, retrieved from STN Database accession No. 2003:646599 abstract; compounds 579545-52-1, (2003).

\* cited by examiner

US 11,214,593 B2

```
                         SEQUENCE LISTING

<160> NUMBER OF SEQ ID NOS: 7

<210> SEQ ID NO 1
<211> LENGTH: 7
<212> TYPE: PRT
<213> ORGANISM: Artificial
<220> FEATURE:
<223> OTHER INFORMATION: PEPTIDE
<220> FEATURE:
<221> NAME/KEY: MOD_RES
<222> LOCATION: (7)..(7)
<223> OTHER INFORMATION: AMIDATION

<400> SEQUENCE: 1

Cys Phe Glu Ile Ser Lys Tyr
1               5

<210> SEQ ID NO 2
<211> LENGTH: 7
<212> TYPE: PRT
<213> ORGANISM: Artificial
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 2

Cys Phe Glu Val Ser Lys Tyr
1               5

<210> SEQ ID NO 3
<211> LENGTH: 7
<212> TYPE: PRT
<213> ORGANISM: Artificial
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 3

Cys Phe Glu Ile Ser Lys Tyr
1               5

<210> SEQ ID NO 4
<211> LENGTH: 6
<212> TYPE: PRT
```

-continued

```
<213> ORGANISM: Artificial
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 4

Phe Glu Ile Ser Lys Tyr
1               5

<210> SEQ ID NO 5
<211> LENGTH: 6
<212> TYPE: PRT
<213> ORGANISM: Artificial
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 5

Val Phe Ser Thr Ala Leu
1               5

<210> SEQ ID NO 6
<211> LENGTH: 7
<212> TYPE: PRT
<213> ORGANISM: Artificial
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 6

Cys Val Phe Ser Thr Ala Leu
1               5

<210> SEQ ID NO 7
<211> LENGTH: 16
<212> TYPE: PRT
<213> ORGANISM: Artificial
<220> FEATURE:
<223> OTHER INFORMATION: PEPTIDE
<220> FEATURE:
<221> NAME/KEY: misc_feature
<222> LOCATION: (1)..(1)
<223> OTHER INFORMATION: X represents (Cys)a, wherein a is 0 or 1
<220> FEATURE:
<221> NAME/KEY: misc_feature
<222> LOCATION: (2)..(2)
<223> OTHER INFORMATION: X represents (Cys)b, wherein b is 0 or 1
<220> FEATURE:
<221> NAME/KEY: misc_feature
<222> LOCATION: (3)..(3)
<223> OTHER INFORMATION: X represents (Cys)c, wherein c is 0 or 1
<220> FEATURE:
```

```
<221> NAME/KEY: misc_feature
<222> LOCATION: (4)..(4)
<223> OTHER INFORMATION: X represents (Cys)d, wherein d is 0 or 1
<220> FEATURE:
<221> NAME/KEY: misc_feature
<222> LOCATION: (5)..(5)
<223> OTHER INFORMATION: X represents (Cys)e, wherein e is 0 or 1
<220> FEATURE:
<221> NAME/KEY: misc_feature
<222> LOCATION: (8)..(8)
<223> OTHER INFORMATION: X represents any amino acid
<220> FEATURE:
<221> NAME/KEY: misc_feature
<222> LOCATION: (12)..(12)
<223> OTHER INFORMATION: X represents (Cys)f, wherein f is 0 or 1
<220> FEATURE:
<221> NAME/KEY: misc_feature
<222> LOCATION: (13)..(13)
<223> OTHER INFORMATION: X represents (Cys)g, wherein g is 0 or 1
<220> FEATURE:
<221> NAME/KEY: misc_feature
<222> LOCATION: (14)..(14)
<223> OTHER INFORMATION: X represents (Cys)h, wherein h is 0 or 1
<220> FEATURE:
<221> NAME/KEY: misc_feature
<222> LOCATION: (15)..(15)
<223> OTHER INFORMATION: X represents (Cys)i, wherein i is 0 or 1
<220> FEATURE:
<221> NAME/KEY: misc_feature
<222> LOCATION: (16)..(16)
<223> OTHER INFORMATION: X represents (Cys)j, wherein j is 0 or 1

<400> SEQUENCE: 7

Xaa Xaa Xaa Xaa Xaa Phe Glu Xaa Ser Lys Tyr Xaa Xaa Xaa Xaa Xaa
1               5                   10                  15
```

ANTICANCER PEPTIDES AND USES THEREOF

This application claims the benefit of European Patent Application EP17382667 filed on Oct. 5, 2017.

SEQUENCE LISTING

The instant application contains a Sequence Listing which has been filed electronically in ASCII format and is hereby incorporated by reference in its entirety. Said ASCII copy, created on Dec. 18, 2020, is named P3947PC00_filing_ST2520201218.txt and is 3,116 bytes in size.

TECHNICAL FIELD

The present invention relates to the field of antineoplastic compounds, in particular to anticancer peptides and anticancer compositions comprising said peptides. The invention also relates to the use of said peptides and said compositions for the prophylactic or therapeutic treatment of pancreatic cancer.

BACKGROUND ART

The therapeutic use of proteins and peptides that act intracellularly holds much promise for the treatment of cancer and other diseases.

Cancer is a group of diseases involving abnormal cell growth with the potential to invade or spread to other parts of the body. Cancer is a multifactorial disease, i.e. it is the result of the occurrence of multiple factors. Said factors usually converge in the generation of mutations in proto-oncogenes that cause cellular proliferation to increase. Mutations may also occur in tumor suppressor genes whose normal function is to regulate cellular proliferation. Mutations may also occur in DNA repair enzymes, impairing the ability of the cell to repair damage before proliferating therefore generating genomic instability.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Each of these therapies has varying degrees of efficacy and is accompanied with varying side effects. These side effects, together with the multidrug resistance already disclosed for traditional chemotherapy, have prompted urgent needs for novel anticancer drugs or therapeutic approaches.

One particularly deadly type of cancer is pancreatic cancer. This type of cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

The most common symptoms of pancreatic cancer include jaundice, abdominal pain, and weight loss, which, together with other presenting factors, are nonspecific in nature. Thus, diagnosing pancreatic cancer at an early stage of tumor growth is often difficult and requires extensive diagnostic work-up, often times including exploratory surgery. Endoscopic ultrasonography and computed tomography are the best noninvasive means available today for diagnosis of pancreatic cancer. However, reliable detection of small tumors, as well as differentiation of pancreatic cancer from focal pancreatitis, is difficult. The vast majority of patients with pancreatic cancer are presently diagnosed at a late stage when the tumor has already extended outside of the capsule to invade surrounding organs and/or has metastasized extensively. Late detection of the disease is common, and early pancreatic cancer diagnosis is rare in the clinical setting.

Current treatment procedures available for pancreatic cancer have not led to a cure, nor to a substantially improved survival time. Surgical resection has been the only modality that offers a chance at survival. However, due to a large tumor load, only 10% to 25% of patients are candidates for "curative resection". For those patients undergoing a surgical treatment, the five-year survival rate is still poor, averaging only about 10%. Therefore, pancreatic cancer is one of the types of cancer where there is a higher need of development of efficient therapies.

One of the most promising therapeutic alternatives against cancer currently under development are anticancer peptides. These peptides have several important advantages over traditional anticancer agents such as high activity, specificity and affinity, and minimal drug-drug interaction. They can be used in combination with surgical resection. They also present several advantages with respect to therapies based on proteins or antibodies—they are small in size, easy to synthesize, they have the ability to penetrate the cell membranes, and have minimal biological and chemical diversity. An added benefit of using peptides as a treatment is that they do not accumulate in specific organs (e.g. kidney or liver), which can help to minimize their toxic side effects. They can also be rapidly synthesized and easily modified and are less immunogenic than recombinant antibodies or proteins. All these characteristics make peptide therapeutics a promising field for emerging anticancer agents.

However, therapeutic peptides do have some significant drawbacks such as low stability or resistance to proteases, which has hindered their development and arrival to the clinic.

Therefore, in spite of the efforts made, there continues to be a need in the clinical field of neoplastic diseases for therapeutic alternatives, such as effective anticancer peptides.

SUMMARY OF INVENTION

The present inventor has developed various peptides with the capacity to inhibit the growth of cancer cells. Surprisingly, the inventor has found that the presence of at least one cysteine residue in a terminal end confers the peptides of the invention a potent cancer inhibitory activity. Importantly, the peptides provided herein also display high solubility and high stability in frozen solutions, which makes them suitable for therapeutic compositions. All these characteristics make the peptides of the invention an important pharmacological alternative in the treatment of yet practically incurable tumors, like pancreatic tumors.

In a first aspect, the present invention provides a peptide of formula (I) or a pharmaceutically acceptable salt thereof, $$C_a C_b C_c C_d C_e \text{FEX}_1 \text{SKYC}_f C_g C_h C_i C_j \qquad \text{(I) (SEQ ID NO: 7)}$$

wherein:
the N-terminal group of the peptide is a monoradical of formula —$NHR_1$,
the C-terminal group of the peptide is a monoradical of formula —$C(O)$—$R_2$;

R₁ is a monoradical selected from hydrogen and —C(O)—(C₁-C₂₀)alkyl;

R₂ is a monoradical selected from —OH and —NR₃R₄ radical;

R₃ and R₄ are independently selected from hydrogen and (C₁-C₁₀)alkyl;

"a" to "j" are integers from 0 to 1, provided that at least one of "a" to "j" is 1; and X₁ represents any amino acid.

As it is shown below, the peptides of the invention are highly specific, being capable of specifically target cancer cells. That is, the peptides of the invention are able to "discriminate" between normal and cancer cells. This means a great advance in the field of cancer because one of the most widely known side-effects of current anti-cancer therapies is the side-effects due to their lack of specificity. This specificity towards cancer cells also explains the experimental data provided below, supporting the non-toxicity of said peptides when they are administered to various types of human primary cells.

These properties make the peptides of formula (I) of the invention suitable as cancer therapeutics.

In a second aspect, the invention relates to a conjugate comprising the peptide according to the first aspect.

A third aspect of the invention relates to a pharmaceutical composition comprising a therapeutically effective amount of the peptide of formula (I) or a pharmaceutically acceptable salt thereof of the first aspect, or a conjugate of the second aspect, with at least one pharmaceutically acceptable excipient, diluent or carrier.

A fourth aspect of the invention relates to the peptide, the conjugate, or the pharmaceutical composition of the invention for use as a medicament.

And, finally, in a fifth aspect the present invention provides the peptide, the conjugate or pharmaceutical composition of the invention for use in the treatment or prevention of a neoplastic disease.

DETAILED DESCRIPTION OF THE INVENTION

Figure 1:
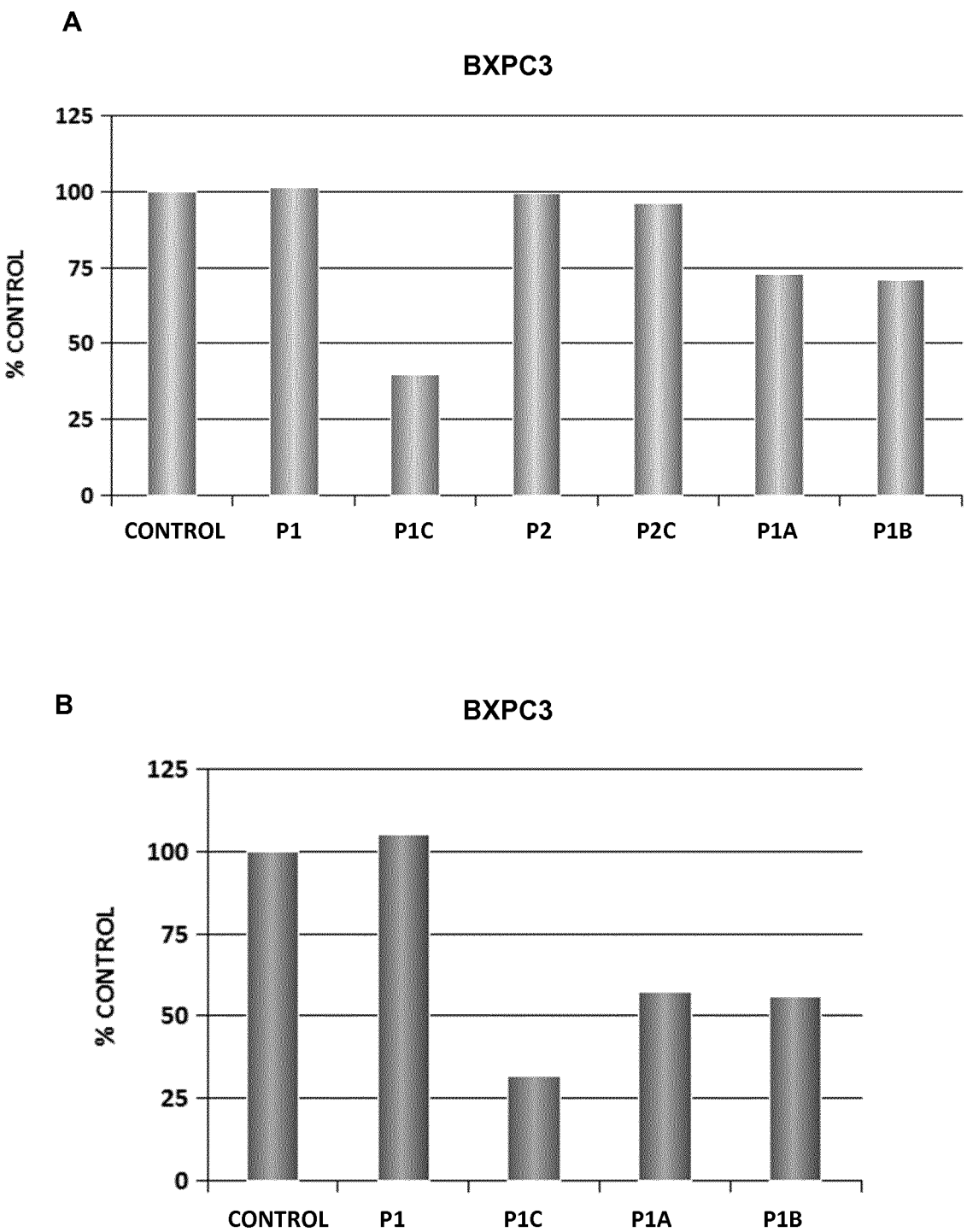
FIG. 1, related to Assay 1, are two bar diagrams showing the inhibitory effect of various peptides of the invention at two different concentrations on the growth of human pancreatic tumor cells (BXPC3) in comparison to mock treated cells. The y-axis represents the number of cells after 72 h of treatment as a percentage of the number of mock treated cells, which is accorded a 100% value. (A) Cells were treated with peptides at 20 μM concentration. The first column (CONTROL), corresponds to mock treated cells, the second column (P1) (SEQ ID NO: 4) corresponds to the P1 peptide wherein the N-terminal end is acetylated and the C-terminal end is amidated; the third column (P1C) (SEQ ID NO: 3), corresponds to a variant of the P1 peptide with a terminal cysteine wherein the N-terminal end is acetylated and the C-terminal end is amidated; the fourth column (P2) (SEQ ID NO: 5) correspond to the P2 peptide wherein the N-terminal end is acetylated and the C-terminal end is amidated; the fifth column (P2C) (SEQ ID NO: 6), corresponds to a variant of the P2 peptide with a terminal cysteine wherein the N-terminal end is acetylated and the C-terminal end is amidated; the sixth column (P1A) (SEQ ID NO: 1) corresponds to a variant of the P1C peptide wherein the N-terminal end is free (not acetylated) and the C-terminal end is amidated; and the seventh column (P1B) (SEQ ID NO: 2) corresponds to a variant of the P1C peptide wherein the N-terminal end is acetylated, the C-terminal end is amidated, and the isoleucine is substituted by a valine. (B) Cells were treated with peptides at 40 μM concentration. The first column (CONTROL), corresponds to mock treated cells, the second, third, fourth, and fifth columns correspond to cells treated with the P1, P1C, P1A, and P1B peptides, respectively. The sequences of the peptides are further detailed in Example 2.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As above exposed, the inventors propose a set of peptides of formula (I) or pharmaceutically acceptable salts thereof with potent cancer inhibitory activity.

As used herein, the term "pharmaceutically acceptable salt", when referred to the peptide of the invention, refers to those salts which are, within the scope of sound medical judgment, suitable for use in contact with the tissues of humans and non-human animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

In the present invention, the term "amino acid" refers to a molecule containing both an amino group and a carboxyl group.

Suitable amino acids include, without limitation, alpha amino acids, such as the L-isomers of alpha-amino acids of the 20 common naturally occurring alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; natural beta-amino acids (e.g., beta-alanine); and unnatural amino acids.

The term "unnatural amino acid" comprises D-isomers of the 20 common naturally occurring alpha-amino acids or amino acids of formula (A)

(A)

wherein R and R' have the meaning provided in Table 1 below.

| Exemplary unnatural alpha-amino acids | Suitable amino acid side chains | |
| --- | --- | --- |
| | R | R' |
| D-Alanine | —H | —$CH_3$ |
| D-Arginine | —H | —$CH_2CH_2CH_2$—NHC(=NH)$NH_2$ |
| D-Asparagine | —H | —$CH_2C$(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2C$(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2Ph$ |
| D-Proline | —H | -2-(pyrrolidine) |
| D-Serine | —H | —$CH_2OH$ |
| D-Threonine | —H | —$CH_2CH(OH)(CH_3)$ |
| D-Tryptophan | —H | —$CH_2$-3-(1H-indole) |
| D-Tyrosine | —H | —$CH_2$-(p-hydroxyphenyl) |
| D-Valine | —H | -isopropyl |
| Di-vinyl | —CH=$CH_2$ | —CH=$CH_2$ |

| Exemplary unnatural alpha-amino acids | R and R' are equal to: | |
| --- | --- | --- |
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2C$(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2C$(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |

Further illustrative non-limitative examples of unnatural amino acids are summarized in Table 2:

TABLE 2

| Three letter code | Amino acid |
| --- | --- |
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4 Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| alle | allo-Isoleucine |
| Nva | Norvaline |
| Nle | Norleucine |
| Orn | Ornithine |

Each one of the amino acids forming the peptide of the invention can have, independently from the others, L- or D-configuration.

Amino acids used in the preparation of the peptides of the present invention may be prepared by organic synthesis, or obtained by other routes, such as, for example, degradation of or isolation from a natural source.

In one particular embodiment of the first aspect, optionally in combination with any embodiments provided above or below, $X_1$ is selected from the amino acids Ala, Ile, Leu, Phe, Val, Pro, and Gly. More particularly, $X_1$ is Ile or Val. Even more particularly, $X_1$ is Ile.

In another particular embodiment of the first aspect, optionally in combination with any embodiments provided above or below, $R_1$ is —C(O)($C_1$-$C_{10}$)alkyl. More particularly, $R_1$ is —C(O)($C_1$-$C_5$)alkyl. Even more particularly, $R_1$ is —C(O)—$CH_3$.

In another particular embodiment of the first aspect, optionally in combination with any embodiments provided above or below, $R_2$ is —$NR_3R_4$. More particularly, $R_3$ and $R_4$ are the same or different and are selected from hydrogen and ($C_1$-$C_5$)alkyl.

In the present invention the term "alkyl" encompasses both lineal and branched hydrocarbon chains.

Illustrative non-limitative examples of "alkyl" are: methyl (C1), ethyl (C2), propyl (C3), isopropyl (C3), isobutyl (C4), sec-butyl (C4), tert-butyl (C4), pentyl (C5), hexyl, (C6), heptyl (C7), octyl (C9), nonyl (C9), and decyl (C10), among others.

Yet in another particular embodiment, optionally in combination with any embodiments above or below, one of "a" to "j" is 1 and the others are 0. In particular "a" is 1 and "b", "c", "d", "e", "f" "g", "h", "i" and "j" are 0.

Another particular embodiment of the first aspect comprises a peptide selected from the group consisting of sequences SEQ ID NO: 1 to SEQ ID NO: 3, which are summarized in Table 3.

TABLE 3

| Peptide | SEQ ID | Sequence |
| --- | --- | --- |
| P1A | SEQ ID NO: 1 | CFEISKY-$NH_2$ |
| P1B | SEQ ID NO: 2 | $CH_3$-C(O)-CFEVSKY-$NH_2$ |
| P1C | SEQ ID NO: 3 | $CH_3$-C(O)-CFEISKY-$NH_2$ |

The peptides of the present invention can be prepared following routine protocols such as by solid phase synthesis, wherein successive steps of (a) deprotecting the amino acid to be bound, and (b) protected-amino acid coupling cycles are performed.

The protecting group can be an N-protecting group, C-protecting group or a side-chain protecting group. There are commercially available protecting groups belonging to all three categories.

Illustrative non-limitative examples of amino acid protecting groups are the N-protecting groups t-Boc (or Boc) and Fmoc. When t-Boc or Fmoc is used in the synthesis of a peptide, the main four steps are: (a) protecting group is removed from the trailing amino acids (commercially available) in a deprotection reaction; (b) deprotection reagents are washed away to provide a clean coupling environment, (c) protected amino acids dissolved in a solvent such as dimethylformamide (DMF) combined with coupling reagents are pumped through the synthesis column, and (d) coupling reagents are washed away to provide clean deprotection environment. Depending on the particular N-protecting group, the deprotection reagent and the coupling reagent is one or another. The skilled person in the art, based on his general knowledge, and by routine methods, can optimize the particular conditions, if necessary.

Alternatively, the peptides of the invention can be obtained by means of recombinant DNA technology.

As above described, the second aspect of the present invention relates to a conjugate comprising the peptide of the first aspect. More particularly, the conjugate comprises a cell penetrating element. Even more particularly, the cell penetrating element is a cell penetrating peptide (CPP).

The term "conjugate" as used herein refers to a compound that has been formed by the joining of a peptide of the invention with one or more compounds via either a covalent or non-covalent bond.

In the present invention the term "cell penetrating peptide" ("CPP") refers to short peptides that facilitate cellular uptake of various molecular cargos (from nanosize particles to small chemical molecules and large fragments of DNA). The "cargo" is associated to peptides via the C(t) or N(t), either through chemical linkage via covalent bonds or through non-covalent interactions. The function of the CPPs are to deliver the cargo into cells, a process that commonly occurs through endocytosis with the cargo delivered to delivery vectors for use in research and medicine. Current use is limited by a lack of cell specificity in CPP-mediated cargo delivery and insufficient understanding of the modes of their uptake. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only nonpolar residues, with low net charge or have hydrophobic amino acid groups that are crucial for cellular uptake. The conjugation of the CPP to the peptide provided in the present invention can be performed following well-known routine protocols, such as solid phase synthesis or solution selective capping. (cf. Copolovici D. M. et al., "Cell-Penetrating Peptides: Design, Synthesis, and Applications", 2014, ACS Nano, 2014,8 (3), pp 1972-1994).

Virtually any cell penetrating peptide with capacity to internalize a peptide in a cell can be used; nevertheless, in a particular embodiment, said carrier peptide is a peptide comprising a "PTD" ("protein transduction domain") segment. Illustrative non-limiting examples of proteins comprising protein transduction domains (PTDs) include the human immunodeficiency virus 1 (HIV-1) TAT ("transacting translational protein") protein, the Drosophila antennapedia homeotic transcription factor (Antp) and the herpesvirus simplex 1 (HSV-1) VP22 DNA-binding protein, although it has also been suggested that other proteins have this property of internalizing peptides in cells, such as influenza virus hemagglutinin, lactoferrin, fibroblast growth factor-1, fibroblast growth factor-2 and the Hoxa-5, Hoxb-4 and Hoxc-8 proteins (Ford K. G. et al., Gene Therapy, 2001; 8:1-4).

The peptide of the invention can be bound to any one of the (amino or carboxyl) terminal ends of the carrier peptide with capacity to internalize a peptide of the invention in a cell. Therefore, in a particular embodiment, the carboxyl-terminal end of the peptide of the invention is bound to the amino-terminal end of said carrier peptide, whereas in another particular embodiment, the amino-terminal end of the peptide of the invention is bound to the carboxyl-terminal end of said carrier peptide.

The peptide of the invention may or may not be directly bound to the cell penetrating peptide. Therefore, in a particular embodiment, optionally in combination with any one of the embodiments provided above or below, the peptide of the invention is directly bound to the cell penetrating peptide. In another embodiment, optionally in combination with any one of the embodiments provided above or below, the conjugate of the second aspect of the invention further comprises a spacer peptide located between the peptide as defined in the first aspect of the invention and the cell penetrating peptide. Said spacer peptide is advantageously a peptide with structural flexibility, such as a peptide giving rise to a non-structured domain. Virtually any peptide with structural flexibility can be used as a spacer peptide; nevertheless, illustrative non-limiting examples of said spacer peptides include peptides containing repeats of amino acid moieties, e.g., of Gly and/or Ser, or any other suitable repeat of amino acid moieties.

In another embodiment of the second aspect of the invention, the cell penetrating agent is a nanoparticle delivery system, which is known to be biocompatible and protect the active ingredient from degradation.

The term "nanoparticle" as used herein, refers to a particle with at least two dimensions at the nanoscale, particularly with all three dimensions at the nanoscale, where the nanoscale is the range about 1 nm to about 300 nm. Particularly, when the nanoparticle is substantially rod-shaped with a substantially circular cross-section, such as a nanowire or a nanotube, the "nanoparticle" refers to a particle with at least two dimensions at the nanoscale, these two dimensions being the cross-section of the nanoparticle.

Biodegradable nanoparticle delivery systems that increase intracellular uptake, e.g., polymeric and surface modified nanoparticles as described in US 2009/0136585 and, can also be used. Examples include poly DL-lactide-co-gly-colide (PLGA) nanoparticles, e.g., surface-modified with known surface-modifying agents, such as heparin, dodecyl-methylammonium bromide (DMAB), DEAE-Dextran, lipofectin, and fibrinogen, among others The term "lipidic nanoparticle" as used herein, refers to a nanoparticle whose membrane is totally made of lipids. Suitable lipids include, without limitation, phospholipids such as phosphatidylcholines ("PC's"), phosphatidylethanolamines ("PE's"), phosphatidylserines ("PS's"), phosphatidylglycerols ("PG's"), phosphatidylinositols ("PI's") and phosphatidic acids ("PA's"). Such phospholipids generally have two acyl chains, these being either both saturated, both unsaturated or one saturated and one unsaturated; said chains include, without limitation: myristate, palmitate, stearate, oleate, linoleate, linolenate, arachidate, arachidonate, behenate and lignocerate chains. Phospholipids can also be derivatized, by the attachment thereto of a suitable reactive group. Such a group is generally an amino group, and hence, derivatized phospholipids are typically phosphatidylethanolamines. The different moieties suited to attachment to PE's include, without limitation: acyl chains, useful for enhancing the fusability of liposomes to biological membranes; peptides, useful for destabilizing liposomes in the vicinity of target cells; biotin and maleimido moieties, useful for linking targeting moieties such as antibodies to liposomes; and various molecules such as gangliosides, polyalkylethers, polyethylene glycols and organic dicarboxylic acids. Other lipids which can constitute the membrane of the nanoparticle include, but are not limited to, cholesterol and 1,2-Dioleoyl-sn-Glycero-3-Phosphocholine (DOPC).

In one embodiment, the lipidic nanoparticle is selected from the group consisting of liposomes and solid-lipid nanoparticle. In another embodiment, the lipidic nanoparticle is a liposome.

The term "solid lipid nanoparticle" refers to particles, typically spherical, with an average diameter from 10 to 1000 nanometers. Solid lipid nanoparticles possess a solid lipid core matrix that can solubilize lipophilic molecules. The lipid core is stabilized by surfactants (emulsifiers). The term lipid is used here in a broader sense and includes triglycerides (e.g. tristearin), diglycerides (e.g. glycerol bahenate), monoglycerides (e.g. glycerol monostearate), fatty acids (e.g. stearic acid), steroids (e.g. cholesterol), and waxes (e.g. cetyl palmitate). All classes of emulsifiers (with respect to charge and molecular weight) have been used to stabilize the lipid dispersion.

In the present invention, the term "liposome" is to be understood as a self-assembling structure comprising one or more lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

Liposomes can have a single lipid bilayer (unilamellar liposomes,"ULVs"), or multiple lipid bilayers (multilamellar liposomes,"MLVs"or"SPLVs"). Each bilayer surrounds, or encapsulates, an aqueous compartment. Given this encapsulation of aqueous volume within a protective barrier of lipid molecules, liposomes are able to sequester encapsulated molecules, e.g., nucleic acids, away from the degrading effects of factors, e.g., nuclease enzymes, present in the external environment.

Liposomes can have a variety of sizes, e.g., an average diameter as low as 25 nm or as high as 10,000 nm or more. Size is affected by a number of factors, e.g., lipid composition and method of preparation, well within the purview of ordinarily skilled artisans to determine and account for, and is determined by a number of techniques, such as quasi-elastic light scattering, also within the skilled person in the art knowledge.

Various methodologies, also well-known to those skilled in the art, such as sonication, or homogenization, and milling, can be used to prepare liposomes of a smaller size from larger liposomes. Extrusion can be used to size reduce liposomes, that is to produce liposomes having a predetermined mean size by forcing the liposomes, under pressure, through filter pores of a defined, selected size. Tangential flow filtration can also be used to regularize the size of liposomes, that is, to produce a population of liposomes having less size heterogeneity, and a more homogeneous, defined size distribution.

The peptide of the invention can be encapsulated within the particle using well-known methods in the state of the art, such as those disclosed in Tandrup Schmidt S. et al., "Liposome-Based Adjuvants for Subunit Vaccines: Formulation Strategies for Subunit Antigens and Immunostimulators", Pharmaceutics, 2016 Mar. 10;8(1).

The cell-penetrating agents can be further functionalized by conjugating molecules with the ability of recognizing and binding to molecules on tumoral cells' surface.

In one embodiment, the cell-penetrating agent also protects the peptides of the invention against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

If desired, the peptide of the invention can optionally include an amino acid sequence useful for the isolation or purification of the peptide of the invention. Said sequence will be located in a region of the peptide of the invention which does not adversely affect the functionality of the peptide of the invention. Virtually any amino acid sequence which can be used to isolate or purify a protein (generically called tag peptides) can be present in said peptide of the invention. By way of a non-limiting illustration, said amino acid sequence useful for isolating or purifying a protein can be, for example, an arginine tag (Arg-tag), a histidine tag (His-tag), FLAG-tag, Strep-tag, an epitope which can be recognized by an antibody, such as c-myc-tag, SBP-tag, S-tag, calmodulin-binding peptide, cellulose-binding domain, chitin-binding domain, glutathione S-transferase-tag, maltose-binding protein, NusA, TrxA, DsbA, Avi-tag or β-galactosidase, among others.

The peptide of the invention can be obtained by means of a coupling reaction of the peptide of the invention and of the cell penetrating peptide with capacity to internalize a peptide in a cell, which may have been obtained by conventional synthetic methods, such as those which have been previously mentioned (e.g., solid phase chemical synthesis), or by means of recombinant techniques.

A third aspect of the invention relates to a pharmaceutical composition comprising a therapeutically effective amount of the peptide of FORMULA (I), a pharmaceutically acceptable salt thereof, or a conjugate thereof, with at least one pharmaceutically acceptable excipient, diluent or carrier.

The expression "pharmaceutical composition" encompasses both compositions intended for human as well as for non-human animals.

The expression "therapeutically effective amount" as used herein, refers to the amount of the peptide or conjugate that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as colouring agents, coating agents, sweetening, and flavouring agents can be present in the composition, according to the judgment of the formulator.

The pharmaceutical compositions containing the peptide or the conjugate of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

As described above, another aspect of the invention relates to a peptide, a conjugate, or a pharmaceutical composition of the invention for use as a medicament.

In a fifth aspect the present invention provides the peptide, the conjugate, or the pharmaceutical composition of the invention is used in the treatment or prevention of a neoplastic disease, more particularly, in the treatment or prevention of pancreatic cancer. This aspect can also be formulated as the use of the peptide, the conjugate, or the pharmaceutical composition of the invention for the manufacture of a medicament for the treatment or prevention of a neoplastic disease. This aspect can also be formulated as a method for treating or preventing a neoplastic disease, the method comprising administering a therapeutically effective amount of the peptide, the conjugate or the pharmaceutical composition of the invention to a subject in need thereof.

Illustrative non-limiting examples of neoplastic diseases which can be treated with the peptide, conjugate and pharmaceutical composition of the invention include, although they are not limited to, papillomas, adenomas, lipomas, osteomas, myomas, angiomas, nevi, mature teratomas, carcinomas, sarcomas.immature teratomas, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocarcinoma, head and neck cancer, etc. In a particular embodiment of the fifth aspect, the neoplastic disease is pancreatic cancer. From the data herein provided the peptide, conjugate and pharmaceutical composition of the invention may also be useful in the treatment of other diseases such as metabolic, neurologic and inflammatory diseases.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1: Synthesis of the peptides of the invention

Peptides were synthesized by chemical synthesis using solid phase synthesis (SPPS) technology following a classical Fmoc/tBu strategy, either by an automatic peptide synthesizer or manually performed.

The Rink-amide resin was used for the synthesis and for the Fmoc-amino acid couplings N,N'-diisopropylcarbodiimide (DIPCDI) with 1-hydroxybenzotriazole (HOBt) as an additive in dimethylformamide (DMF). Deprotection was carried out with a solution of 20% piperidine in DMF.

In the case of the acetylated sequences, the acetylation was carried out in solid phase using a solution of acetic anhydride ($Ac_2O$) with diisopropylethylamine (DIEA) in DMF just before drying the resin. The dried peptidyl resins were treated with a trifluoroacetic acid (TFA) cocktail to cleave the peptide from the resin. The peptide crudes obtained were purified by preparative reverse phase HPLC using a $H_2O$/acetonitrile(can) purification system with TFA and the pure fractions were lyophilized. The results of the HPLC analysis are summarized in Table 4.

TABLE 4

| Peptide | Identification MS spectrum | Peptide purity |
| --- | --- | --- |
| P1 (SEQ ID NO: 4) | 827.6 u.m.a. | 90.54% |
| P1A (SEQ ID NO: 1) | 887.4 u.m.a. | 97.54% |
| P1B (SEQ ID NO: 2) | 915.5 u.m.a. | 97.45% |
| P1C (SEQ ID NO: 3) | 930.7 u.m.a. | 97.00% |
| P2 (SEQ ID NO: 5) | 678.4 u.m.a. | 94.14% |
| P2C (SEQ ID NO: 6) | 781.5 u.m.a. | 99.12% |

Example 2: Cell Culture and Treatment of Cells with the Peptide of the Invention Cell Cultures The BXPC3 cell line from primary adenocarcinoma of human pancreas was provided by the Biomedical Research Institute (IRB) of Barcelona, and human umbilical cord primary endothelial cells (HUVEC) were obtained directly by the investigator and stored in liquid nitrogen in the laboratory. BXPC3 cells were maintained in RPMI-1640 culture medium (Gibco) supplemented with 10% fetal bovine serum and antibiotics. HUVEC cells were maintained in M199 culture medium (Gibco) supplemented with 20% fetal bovine serum, endothelial cell growth supplement (ECGS), Heparin (Hep) and antibiotics. Cultures were maintained in the cell incubator in a humid atmosphere at 37° C. containing 5% $CO_2$.

The different peptides to be tested were easily dissolved in DMSO at a concentration of 50 mM and subsequently a 5 mM intermediate dilution was prepared in Dulbecco's PBS which was subjected to two short cycles of sonication, which retendered the peptides completely soluble. From this latter dilution, the different treatments at 10, 20, 30, and 40 uM concentrations were prepared in supplemented medium. The different treatments were prepared at a double concentration and 100 μl of them were added to the same volume of cell growth medium in the wells to reach the final concentrations above disclosed.

Cell Treatments

Assays with the different peptides were performed following the protocol explained below. The cells were resuspended by trypsin/EDTA digestion with Trypsin 0,25%-EDTA in the case of BXPC3 cells, and Trypsin 0,25%-EDTA in the case of HUVEC cells. Once resuspended in culture medium, they were counted in Newbauer's chamber after a 1:1 dilution with trypan blue. This staining allows the number of living cells in the suspension to be known. From the counting, a suitable dilution of the cells (5000 cells/100 μl/well for BXPC3 and 10000 cells/100 μl/well for HUVEC) was prepared. Cells were left 24 hours in culture within the cell incubator. After 24 hours of incubation, 100 μl/well of a double concentrated solution of the peptides prepared as explained above were added. Treatments were maintained for 72 hours by keeping the cells in the cell incubator. The sequences of the peptides used in the assay are shown in Table 5.

TABLE 5

| Peptides of the invention | Sequence | SEQ ID NO: |
| --- | --- | --- |
| P1A | CFEISKY-NH$_2$ | SEQ ID NO: 1 |
| P1B | CH$_3$-C(O)-CFEVSKY-NH$_2$ | SEQ ID NO: 2 |
| P1C | CH$_3$-C(O)-CFEISKY-NH$_2$ | SEQ ID NO: 3 |
| Peptides for comparative purposes | Sequence | SEQ ID NO: |
| P1 | CH$_3$-C(O)-FEISKY-NH$_2$ | SEQ ID NO: 4 |
| P2 | CH$_3$-C(O)-VFSTAL-NH$_2$ | SEQ ID NO: 5 |
| P2C | CH$_3$-C(O)-CVFSTAL-NH$_2$ | SEQ ID NO: 6 |

After 72 hours, the culture media was removed by decantation, cells were washed twice with DPBS and then cells were fixed with 100 μl of 4% paraformaldehyde solution for 30 min. Two washes were then performed with 100 μl of mQ $H_2O$ and immediately 50 μl of 0.25% Violet Crystal solution, prepared in distilled water, were added and maintained for 30 min at room temperature (RT). At the end of the staining time, several washes with distilled water were performed to completely remove the excess of Violet Crystal, the plates were then completely dried in the oven at 37° C.

The optical density values per well were obtained by a Biotek Synergy™2 multi-detection microplate reader, using a 590 nm filter and by scanning reading, obtaining the mean values per well.

RESULTS

In Vitro Proliferation Assay to Test the Cancer Growth-Inhibitory Activity of the Peptides In order to test the anticancer effect of the peptides of the invention, proliferation assays were conducted onto the human pancreatic tumor cell line BXPC3.

As can be observed in FIG. 1-A, when BXPC3 cells were treated with peptides at 20 μM final concentration, the P1C peptide (SEQ ID NO: 3) reduced cancer cell growth down to 40% in relation to the growth of mock treated cells, which was accorded a 100% value. A remarkable inhibitory capacity of the peptide was still maintained when either the carboxy-terminal acetylation of the P1C peptide was lost—peptide P1A (SEQ ID NO: 1)—or the isoleucine residue was substituted by a valine residue—peptide P1B (SEQ ID NO: 2). When the peptides where applied at 40 μM final concentration (FIG. 1-B) their growth inhibitory effects were even higher.

No inhibition of cancer cell growth was observed for any of the other peptides tested.

Figure 2:
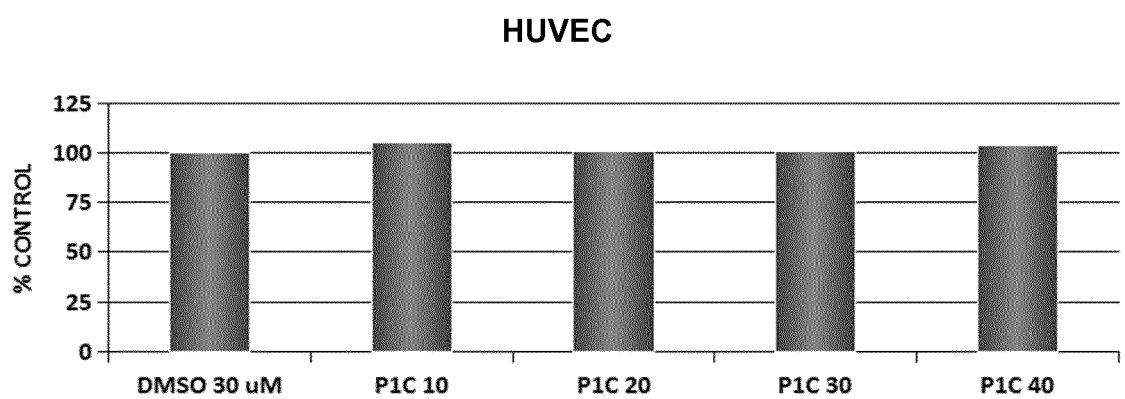
FIG. 2, related to Assay 2, is a bar diagram showing the toxicity effect of the P1C peptide (Ac-CFEISKY-NH₂) (SEQ ID NO: 3) on human umbilical cord primary endothelial cells (HUVEC) at various concentrations in comparison to mock treated cells. The y-axis represents the number of cells after 72 h of treatment as a percentage of the number of mock treated cells (control), which is accorded a 100% value. The first column (DMSO), corresponds to cells treated with the vehicle in which the peptides are dissolved. The second to fifth columns correspond to cells treated with the P1C peptide (SEQ ID NO: 3) at 10, 20, 30, 40 μM concentrations, respectively.

In Vitro Proliferation Assay to Test the Toxicity of the Peptides of the Invention The administration of the peptide P1C (SEQ ID NO: 3)—which presents the highest growth-inhibitory activity in cancer cells (see Assay 1)—did not affect the growth of normal non-transformed cells. The lack of toxicity was maintained independently of the dose of the peptide applied (ranging from 10 μM up to 40 μM final concentration, columns two to five of FIG. 2).

These results unambiguously demonstrate the high therapeutic potential of the peptides of the invention as anticancer agents given their low toxicity in non-transformed cells and their high growth-inhibitory activity in cancer cells.

CITATION LIST

Copolovici D. M. et al., "Cell-Penetrating Peptides: Design, Synthesis, and Applications", ACS Nano, 2014, 8(3): 1972-1994;
Ford K. G. et al., "Protein transduction: an alternative to genetic intervention?" Gene Therapy, 2001; 8:1-4; and
Tandrup Schmidt S. et al., "Liposome-Based Adjuvants for Subunit Vaccines: Formulation Strategies for Subunit Antigens and Immunostimulators", Pharmaceutics, March 2016; 8(1).

The invention claimed is:

1. A peptide of formula (I), or a pharmaceutically acceptable salt thereof consisting of:

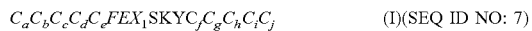  (I)(SEQ ID NO: 7)

$C_a C_b C_c C_d C_e FEX_1 SKYC_f C_g C_h C_i C_j$ wherein:
the N-terminal group of the peptide is a monoradical of formula —$NHR_1$,
the C-terminal group of the peptide is a monoradical of formula —C(O)—$R_2$;
$R_1$ is a monoradical selected from hydrogen and —C(O)—($C_1$-$C_{20}$)alkyl;
$R_2$ is a monoradical selected from —OH and —$NR_3R_4$ radical;
$R_3$ and $R_4$ are independently selected from hydrogen and ($C_1$-$C_{10}$)alkyl;
"a" to "j" are integers from 0 to 1, provided that at least one of "a" to "j" is 1; and
$X_1$ represents any amino acid.

2. The peptide according to claim 1 wherein $X_1$ is selected from Ala, Ile, Leu, Phe, Val, Pro, and Gly.

3. The peptide according to claim 1, wherein $X_1$ is Ile or Val.

4. The peptide according to claim 1, wherein $R_1$ is —C(O)($C_1$-$C_{10}$)alkyl.

5. The peptide according to claim 1, wherein $R_1$ is —C(O)—$CH_3$.

6. The peptide according to claim 1, wherein $R_2$ is $NR_3R_4$.

7. The peptide according to claim 1, wherein $R_3$ and $R_4$ are hydrogen.

8. The peptide according to claim 1, wherein one of "a" to "j" is 1 and the others are 0.

9. The peptide according to claim 1, wherein "a" is 1 and "b", "c", "d", "e", "f", "g" "h", "i" and "j" are 0.

10. The peptide according to claim 1, which is selected from the group consisting of sequences SEQ ID NO: 1 to SEQ ID NO: 3.

11. A pharmaceutical composition comprising a therapeutically effective amount of the peptide of formula (I) or a pharmaceutically acceptable salt thereof as defined in claim 1, with at least one pharmaceutically acceptable excipient, diluent or carrier.

12. A method for treating or preventing a neoplastic disease, the method comprising administering a therapeutically effective amount of the peptide as defined in claim 1 or the pharmaceutical composition as defined in claim 11 to a subject in need thereof.

13. The peptide according to claim 1, wherein $X_1$ is Ile or Val and the C-terminal group of the peptide is a monoradical of formula —C(O)—$NH_2$ or, alternatively, wherein $X_1$ is Ile or Val and the N-terminal group of the peptide is a monoradical of formula —NH—C(O)—$CH_3$; or, alternatively, the C-terminal group of the peptide is a monoradical of formula —C(O)—$NH_2$ and the N-terminal group of the peptide is a monoradical of formula —NH—C(O)—$CH_3$.

14. The peptide according to claim 1, wherein:
one of "a" to "j" is 1 and the others are 0,
$X_1$ is selected from Ile and Val, and
the C-terminal group of the peptide is a monoradical of formula —C(O)—$NH_2$;
or, alternatively,
one of "a" to "j" is 1 and the others are 0,
$X_1$ is selected from Ile and Val,
the N-terminal group of the peptide is a monoradical of formula —NH—C(O)—$CH_3$;
or, alternatively,
one of "a" to "j" is 1 and the others are 0, the C-terminal group of the peptide is a monoradical of formula —C(O)—NH$_2$, and the N-terminal group of the peptide is a monoradical of formula —NH—C(O)—CH$_3$.

15. The peptide according to claim 1, wherein:

"a" is 1 and "b", "c", "d", "e", "f", "g", "h", "i" and "j" are 0,

X$_1$ is selected from Ile and Val, and the C-terminal group of the peptide is a monoradical of formula —C(O)—NH$_2$;

or, alternatively,

"a" is 1 and "b", "c", "d", "e", "f", "g", "h", "i" and "j" are 0,

X$_1$ is selected from Ile and Val, and the N-terminal group of the peptide is a monoradical of formula —NH—C(O)—CH$_3$;

or, alternatively,

"a" is 1 and "b", "c", "d", "e", "f", "g", "h", "i" and "j" are 0, the C-terminal group of the peptide is a monoradical of formula —C(O)—NH$_2$, and the N-terminal group of the peptide is a monoradical of formula —NH—C(O)—CH$_3$.

16. The method for treating or preventing a neoplastic disease, according to claim 12, wherein the cancer is a pancreatic cancer.

\* \* \* \* \*